US007883264B1

(12) United States Patent
Liva

(10) Patent No.: US 7,883,264 B1
(45) Date of Patent: Feb. 8, 2011

(54) METHOD AND APPARATUS FOR PERSONAL PRODUCT DELIVERY

(76) Inventor: Valentino L. Liva, 954 Leonello Ave., Los Altos, CA (US) 94024

( * ) Notice: Subject to any disclaimer, the term of this patent is extended or adjusted under 35 U.S.C. 154(b) by 1051 days.

(21) Appl. No.: 11/235,022

(22) Filed: Sep. 26, 2005

(51) Int. Cl.
*B01F 13/02* (2006.01)
*B01F 15/00* (2006.01)

(52) U.S. Cl. ............... 366/177.1; 366/181.8; 366/182.2; 366/182.3; 366/182.4; 366/191; 366/160.2; 239/413

(58) Field of Classification Search ........................ None
See application file for complete search history.

(56) References Cited

U.S. PATENT DOCUMENTS

| | | | | | |
|---|---|---|---|---|---|
| 5,298,967 | A | * | 3/1994 | Wells | 356/336 |
| 5,520,333 | A | * | 5/1996 | Tofte | 239/10 |
| 5,949,522 | A | * | 9/1999 | Manne | 352/85 |
| 6,169,595 | B1 | * | 1/2001 | Manne | 352/85 |
| 6,615,881 | B2 | * | 9/2003 | Bartholomew et al. | 141/18 |
| 6,622,064 | B2 | * | 9/2003 | Bartholomew et al. | 700/233 |
| 6,627,266 | B2 | * | 9/2003 | Dion | 427/402 |
| 6,932,502 | B2 | * | 8/2005 | Childers et al. | 366/152.1 |
| 2001/0047309 | A1 | * | 11/2001 | Bartholomew et al. | 705/26 |
| 2002/0010528 | A1 | * | 1/2002 | Bartholomew et al. | 700/239 |
| 2002/0016829 | A1 | * | 2/2002 | Defosse | 709/217 |
| 2002/0131985 | A1 | * | 9/2002 | Shana'a et al. | 424/401 |
| 2002/0136700 | A1 | * | 9/2002 | Margosiak et al. | 424/70.21 |
| 2002/0179639 | A1 | * | 12/2002 | Bartholomew et al. | 222/144.5 |
| 2002/0192357 | A1 | * | 12/2002 | Dion | 427/8 |
| 2003/0004403 | A1 | * | 1/2003 | Drinan et al. | 600/301 |
| 2003/0014324 | A1 | * | 1/2003 | Donovan et al. | 705/26 |
| 2003/0090176 | A1 | * | 5/2003 | Bartholomew et al. | 312/35 |
| 2003/0151611 | A1 | * | 8/2003 | Turpin et al. | 345/589 |
| 2004/0004309 | A1 | * | 1/2004 | Sears | 264/325 |
| 2004/0240311 | A1 | * | 12/2004 | Hashiba | 366/101 |
| 2008/0147515 | A1 | * | 6/2008 | Abraham et al. | 705/27 |

FOREIGN PATENT DOCUMENTS

JP         2003-062493       * 3/2003
WO      WO 03/020435      * 3/2003

* cited by examiner

*Primary Examiner*—Tony G Soohoo
(74) *Attorney, Agent, or Firm*—Heimlich Law, PC; Alan Heimlich, Esq.

(57) ABSTRACT

A method and apparatus for personal product delivery have been disclosed.

5 Claims, 12 Drawing Sheets

METHOD AND APPARATUS FOR PERSONAL PRODUCT DELIVERY

FIELD OF THE INVENTION

The present invention pertains to delivery of products. More particularly, the present invention relates to a method and apparatus for personal product delivery.

BACKGROUND OF THE INVENTION

Personal products, for example drugs, perfumes, colognes, aftershave, body sprays, are currently generated in large quantities and distributed to many people. Often these are distributed in quantities that are not fully used. For example, many people waste personal products because they go out of style before they are used up or because they decide they do not like a product after using it once. This presents a problem.

Conversely, while traveling, a user may not be able to bring along all the personal products they desire because of the bulkiness and/or weight of the packaging.

Often, a personal product needs to be customized for an individual in order for it to be most effective. For example, a drug may be most effective if the physical characteristics of the user are taken into account. In another example, the immediate mixing of a combination to produce a targeted pharmaceutical for a specific patient may be needed. Another example may be the necessity for the creation of a drug immediately before use, such as a drug that is made up of various components that degrade over time when combined or a drug whose components tend to react with each other in negative ways or to break down into a less effective drug. However, mass produced drugs are not adjusted. This presents a problem.

BRIEF DESCRIPTION OF THE DRAWINGS

The invention is illustrated by way of example and not limitation in the figures of the accompanying drawings in which.

DETAILED DESCRIPTION

Figure 1:
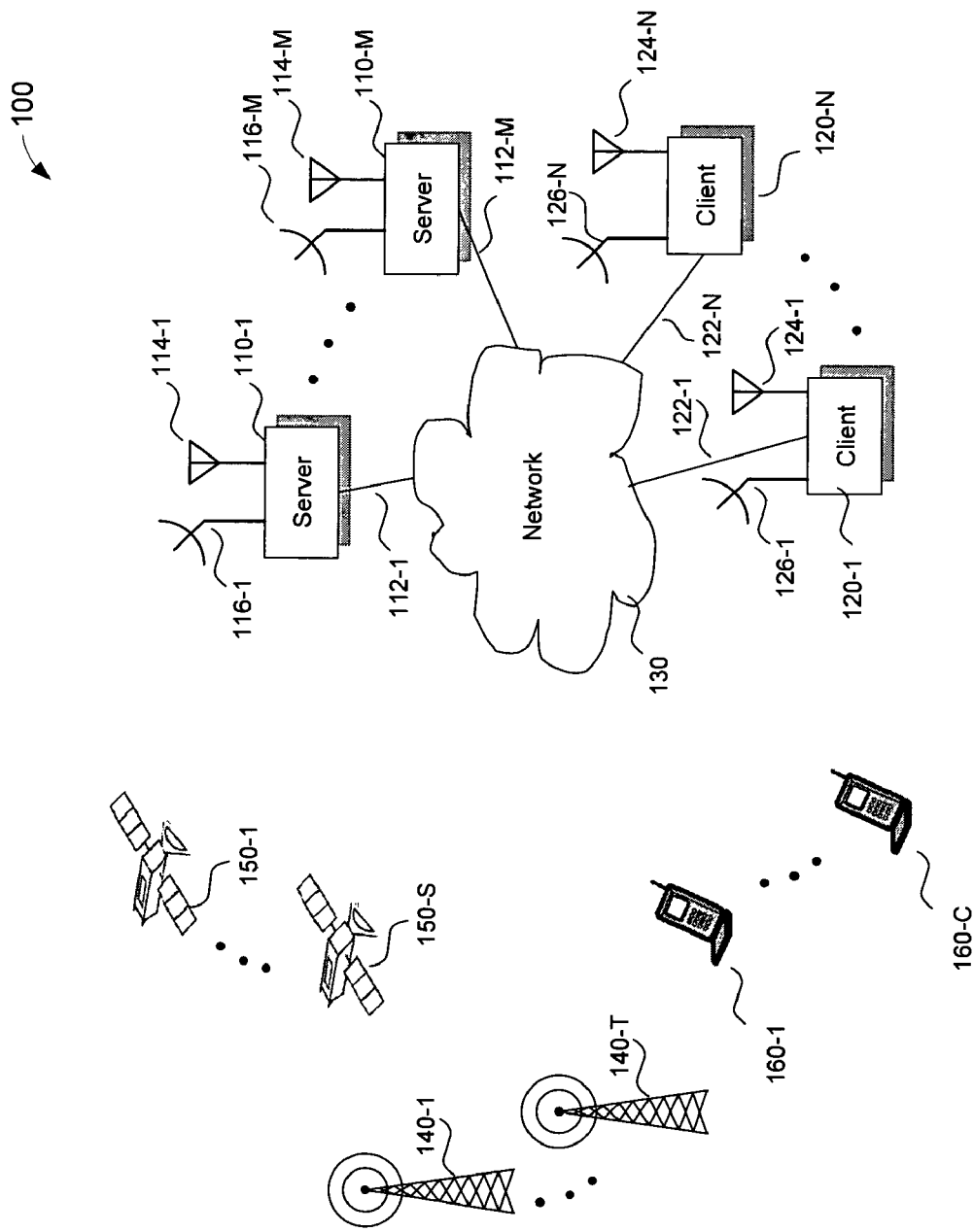
FIG. 1 illustrates a network environment in which the method and apparatus of the invention may be used.

The invention, as exemplified in various embodiments, illustrates personal products delivery ("PPD" or "delivery"). In one embodiment of the invention, PPD is achieved by using microfluidic flow. In other embodiments of the invention, PPD is achieved by using thermal transfer means, electrical transfer means, electrostatic means, etc. Other means are also possible, for example acoustic waves, dielectric wetting, etc.

Personal product delivery may be embodied in a device referred to as a personal product delivery device ("PPDD").

In other embodiments of the invention use is made of other technologies, such as, but not limited to, nanotechnology, micro-electromechanical systems (MEMS), etc. for PPD.

In one embodiment, the invention is a portable device that can deliver personalized products for personal care. In another embodiment, the invention is a device that may be portable, disposable, and/or refillable. In one embodiment of the invention it is capable of synthesizing the personal product for the user by using stored recipes, or formulations defined beforehand by a specialist, or by the user himself. A formulation may be stored into a memory in the PPDD.

In one embodiment of the invention, the control and mixing of fluids for personal delivery may be achieved by using a computerized portable system.

In one embodiment of the invention, it may be used to deliver fragrances in an integrated system capable of delivering personalized perfumes or existing ones that are stored in separate system canisters. The system can combine original fragrances in minute quantities, mix them with additives to allow them to be delivered and dispersed as liquid, droplets, aerosol, or sprayed in the air to expand for the benefit of the user or persons that enjoy such products.

One of skill in the art will appreciate that such an integrated, miniaturized, portable system can also be used in delivering prescription and over-the-counter pharmaceuticals.

There are other uses for the invention as well. For example, such an integrated, miniaturized, portable system can also be used to synthesize new wine compositions from a variety of core wines using only minute elements for wine tasters. Such a possibility allows the preparation in real time of wines from the new "must" produced from freshly crushed grapes. Additionally, the wine compositions and mixing may be done by the user just before dinner or during a meal function according to personal taste, convenience, and/or tolerance to various wines, etc.

In one embodiment of the invention, a product for delivery may be prepared in a form that can be processed by an electronic and/or electromechanical integrated device (for example, MEMS or Microfluidic) and delivered to the user in small calibrated doses.

In one embodiment of the invention, there may be a variety of products available and a selected product may be delivered to a user based on a criteria. For example, a doctor may prescribe a series of medications to be taken in a particular timed order and this information may be programmed into an embodiment of the invention to dispense, or allow access to, the medications in the order prescribed.

In one embodiment of the invention, there may be a variety of compounds available and a final product for delivery may be based on mixing one or more of the compounds together in some predetermined ratio just before delivery. This approach may be very effective where the compounds lose efficacy or are degraded when left mixed for some period of time.

In another embodiment of the invention, doses may be computed to be combined into a mixture of several compounds and combined into one final delivered product following a pre-established formula (i.e. recipe).

In one embodiment of the invention, instructions may be provided to the user for him to decide the combination of compounds in a mixture suitable for his own consumption (new formulation or recipe).

In various embodiments, the PPDD may range from a portable device to a much smaller device. For example, in one embodiment, the PPDD may be a wearable device. In another embodiment, the PPDD may be used for drug delivery and may be an implantable device.

In one embodiment of the invention, the PPDD is a self-contained system that may be constructed as follows. A core MEMS circuit may comprise channels, pumps, mixing chambers, electrical input/outputs (I/Os), and chemical/molecule I/Os and orifices for intake of chemicals/molecules and expelling of finished products. Additional functionalities may be based on the capability to compute and isolate small volumes of chemical/molecules/pre-mixtures for the purpose of delivering the final product and/or to study the synthesized product or drug. The PPDD may be able to process natural, human-made, and synthetic molecules into a final product. The PPDD may contain a microcontroller, a keypad, a battery, a power supply, and an LCD display to guide the user into programming their own products or select pre-established recipes. The PPDD may contain reservoirs of chemicals, molecules, and pre-mixtures for disposable products. The PPDD may be recharged or reloaded with chemicals/molecules/pre-mixtures for non-disposable models. The whole PPDD system may be self-contained, portable, and of credit card dimensions with a thickness of, for example, 5 mm, 10 mm, or 20 mm, etc.

Such a PPDD as described above would allow, for example, an individual to self-administer a dose of an antidote after exposure to a chemical or biological agent or during an allergic reaction.

FIG. 1 illustrates a network environment 100 in which the techniques described may be applied. More details are described below.

Figure 2:
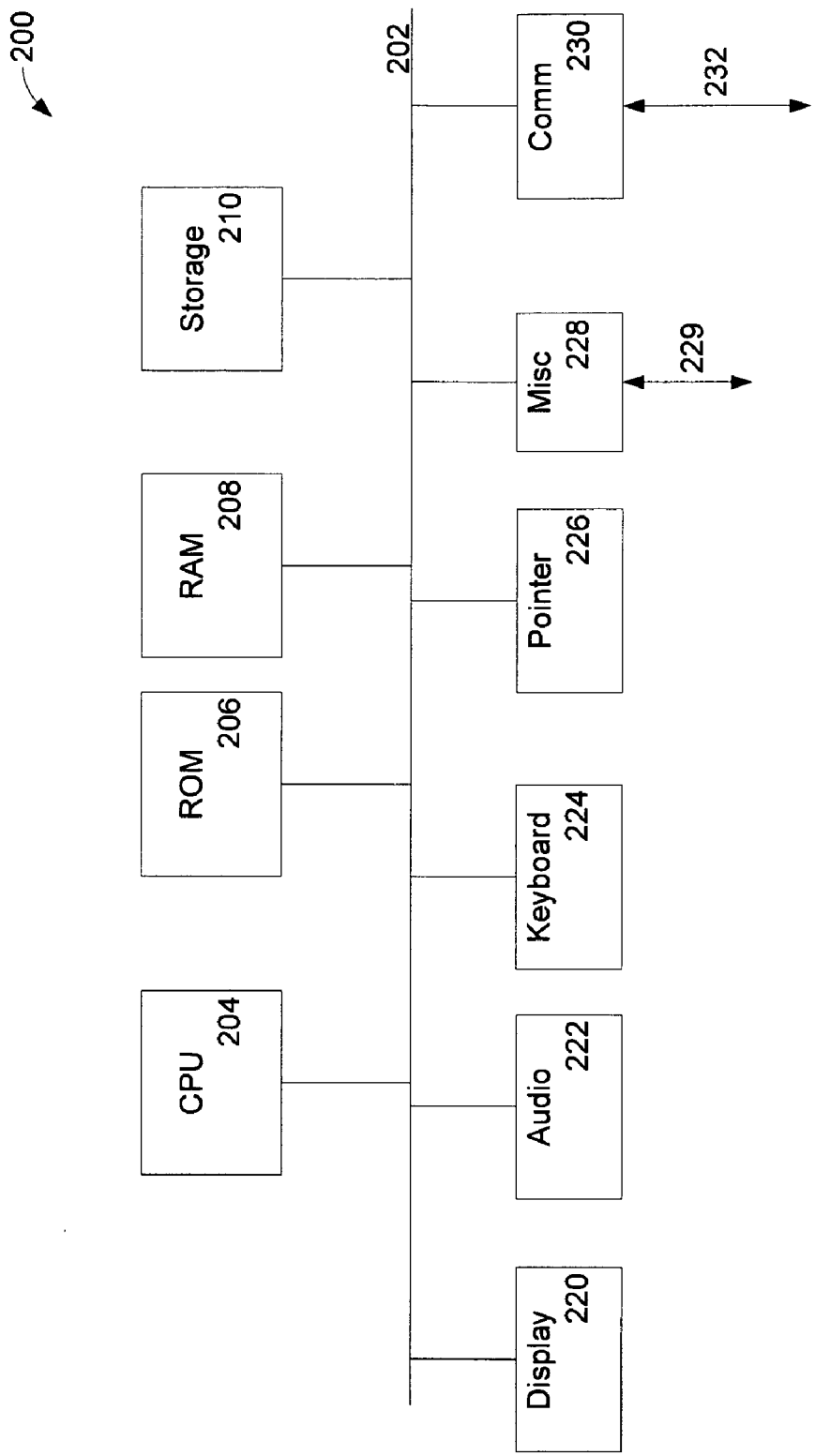
FIG. 2 is a block diagram of a processing system that may be used in some embodiments of the invention.

FIG. 2 illustrates a processing system 200 in block diagram form, which may be representative of a control in a PPDD. More details are described below.

Figure 3:
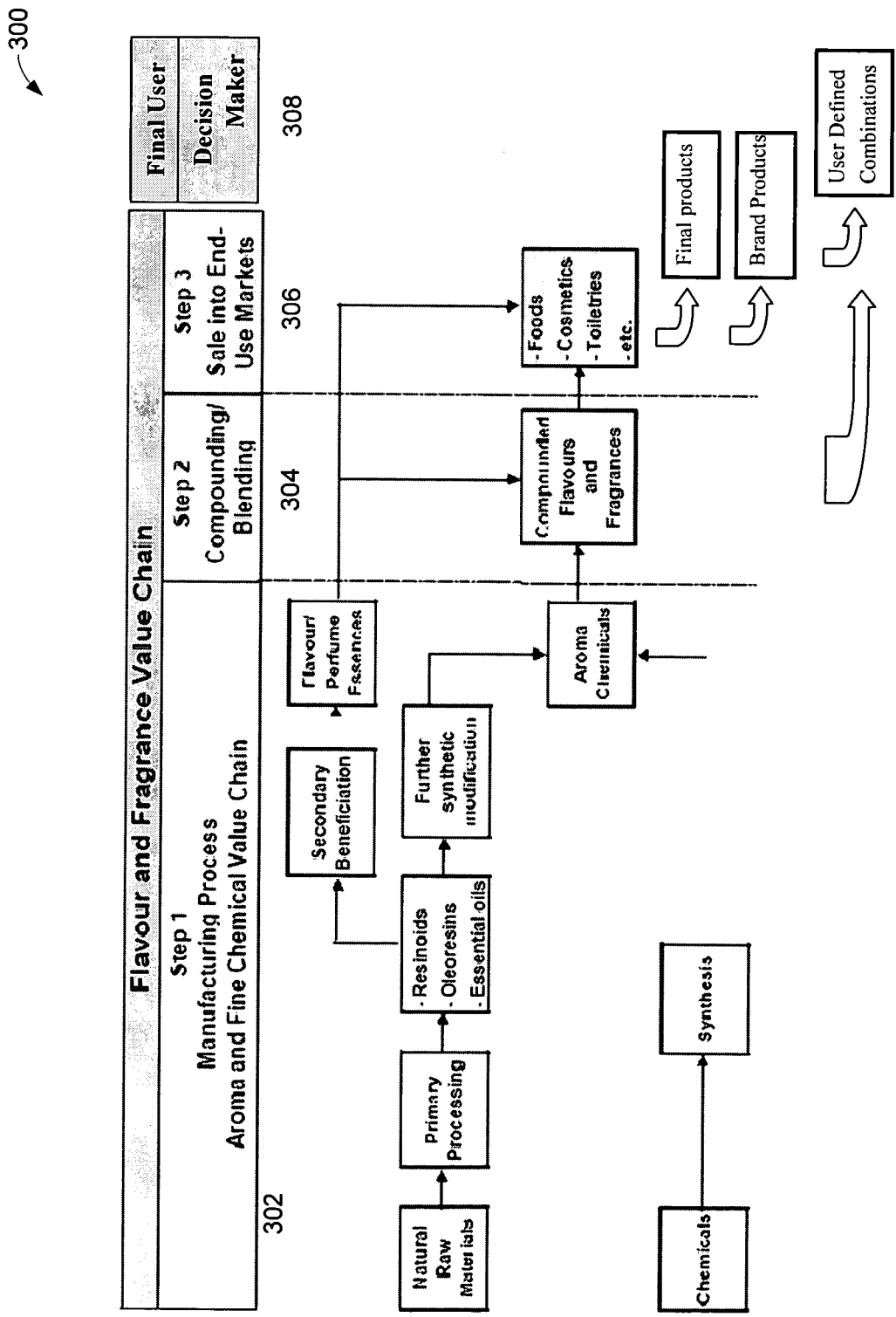
FIG. 3 illustrates an overview where in a chain the present invention may be situated.

FIG. 3 illustrates at 300 an overview of where in a chain the present invention may be situated. At 302 is Step 1, which includes a manufacturing process, for example, for aromas and chemicals. At 304 is Step 2, which is a compounding, blending, or mixing operation. At 306 is Step 3, sale into an end user market, and 308 shows the final user. In one embodiment, the present invention would be situated at Step 2 304 from the standpoint of receiving chemicals from Step 1 302 and blending those chemicals. The PPDD would then be sold into an end market 306 for use by the final user (consumer) 308.

In the embodiment in the environment of FIG. 3, the PPDD may be a computerized delivery system that may contain several creations (chemicals) that may be mixed in small doses, and then delivered to the customer. The PPDD may be easily carried with personal belongings, may be used with discretion, and may be disposable when the creations are depleted.

The PPDD may be the size of a credit card or a calculator and may be adapted to suit consumer tastes. Because the PPDD may be small in size, it may be combined with existing personal systems, such as, but not limited to, cell phones, personal digital assistants (PDAs), iPODs®, etc. For example, a PPDD located in a cell phone may deliver a fragrance to the user based upon a command received from a person on another phone.

Figure 4:
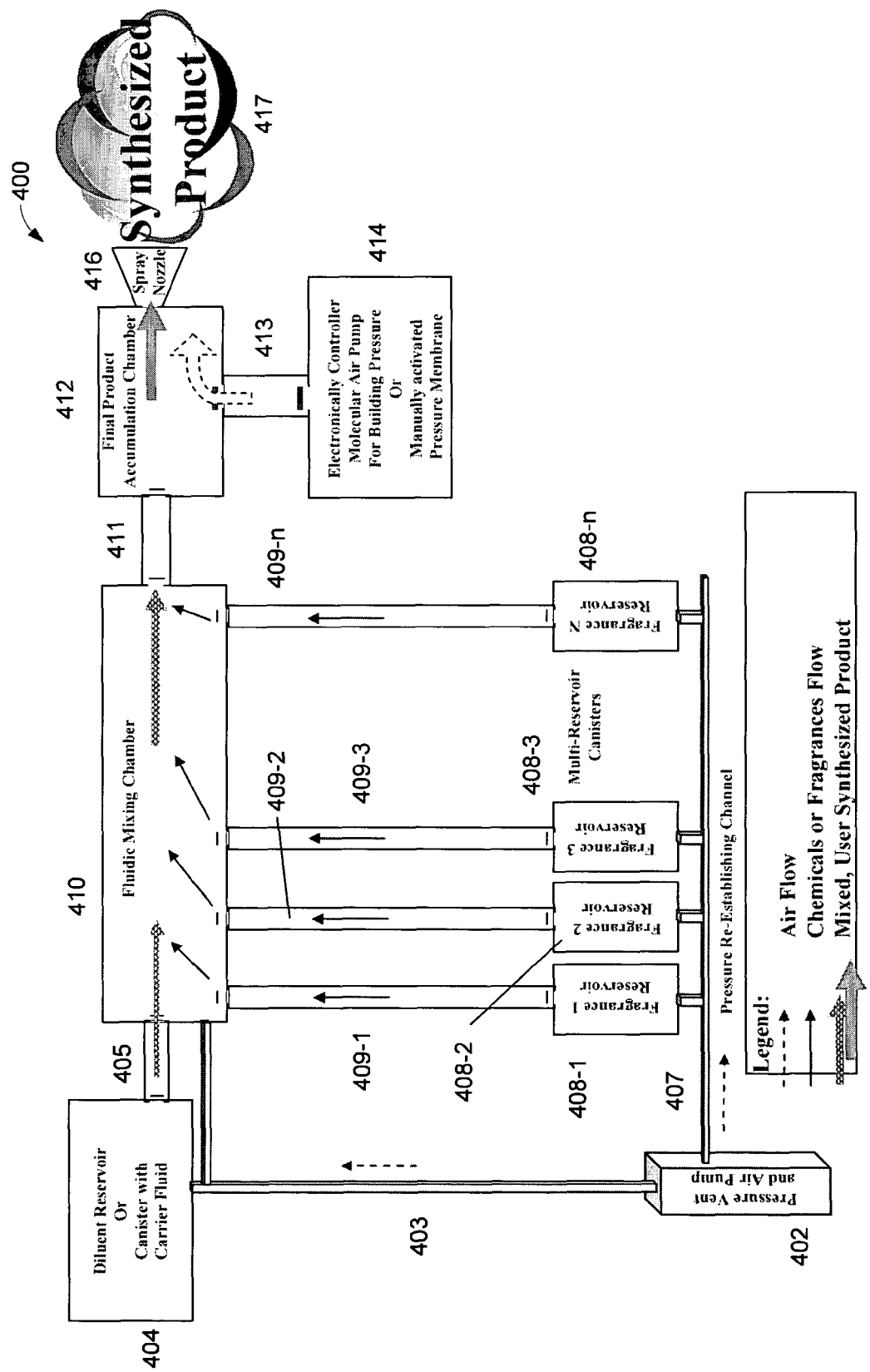
FIG. 4 illustrates one embodiment of the present invention in block diagram form.

FIG. 4 illustrates one embodiment of the present invention 400 in block diagram form. At 402 are a pressure vent and an air pump, which via 403 are in communication with a cartridge, reservoir, or canister containing a diluent, buffer, or carrier fluid 404. The pressure vent and the air pump at 402 are also in communication via 407 with a series of fragrance reservoirs 408-1, 408-2, 408-3, ..., 408-$n$. A reservoir with a diluent or a canister with a carrier fluid 404 via 405 is in communication with a fluidic mixing chamber 410. Mixing chamber 410 is also in communication with fragrance reservoirs 408-1, 408-2, 408-3, ..., 408-$n$ via 409-1, 409-2, 409-3, ..., 409-$n$ respectively. Mixing chamber 410 is in communication via 411 with final product accumulation chamber 412. Final product accumulation chamber 412 via 413 is in communication with 414, an electronically-controlled molecular air pump for building pressure or a manually-activated pressure membrane. Final product accumulation chamber 412 is in communication with spray nozzle 416, which may then deliver the synthesized product 417. Not denoted so as not to obscure the figure, this embodiment may comprise valves as indicated by short lines within 405, within 409-1 through 409-$n$, at the entrance to the fluidic mixing chamber 410 for 409-1 through 409-$n$, at 411, 413, and 412 near 411, and at 412 near 413. These valves control flow in the respective devices where they are located.

In one embodiment of the invention as diagrammed in FIG. 4, the operation is as follows. The Legend indicates the various flows. At 402, pressure is established in 403 and 407. At 404, fluid is forced into 405 and then 410. At the same time, pressure from 407 forces fragrances located in the reservoirs 408-1 to 408-$n$ into the 410, depending upon the valve settings in 409-1 to 409-$n$. The output of the mixing chamber 410 flows through 411 and is combined with a pressure source from 413 and 414. The final product is forced into the spray nozzle 416 and emitted at 417.

Depending upon the settings of the valves, various combinations and volumes of fragrances may be combined. One of skill in the art will appreciate that computer control of the valves is possible and can provide for pre-determined mixing and dispensing of a given volume of mixture.

Figure 5:
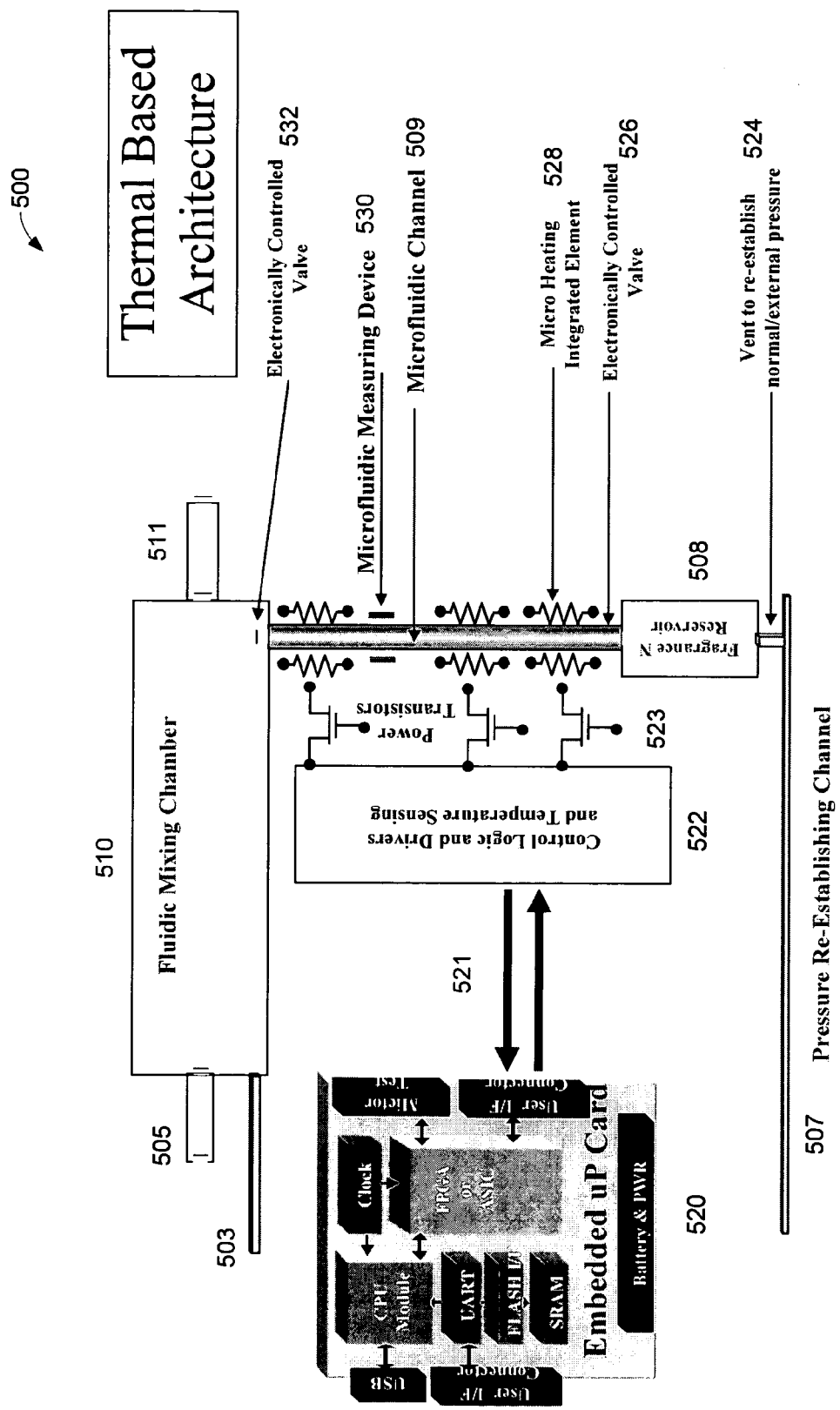
FIG. 5 illustrates one embodiment of the invention showing details for a thermal-based architecture.

FIG. 5 illustrates one embodiment of the invention 500, showing details for a thermal-based architecture. For illustration purposes only, a single fragrance reservoir is shown. At 503 and 507 are pressure channels. 505 is an inlet and 511 is an outlet of fluidic mixing chamber 510. At 520 is a microprocessor for controlling via I/O 512 a control logic block 522, which is connected to a series of power transistors 523, connected to micro heating elements 528. At 524 is a vent, at 526 an electronically controlled valve, at 509 a microfluidic channel, at 530 a microfluidic measuring device, and at 532 an electronically-controlled valve.

FIG. 5 illustrates how a thermal-based architecture may be used to move a fluid, such as a fragrance 508, to a mixing chamber 510. For example, in one embodiment as illustrated in FIG. 5, fluid is moved as follows. The microprocessor controls the heating elements and the valves.

One cycle of "pumping" may consist of the following:
  (a) the heaters 528 are turned off;
  (b) valve 532 is closed;
  (c) valve 526 is opened and channel 509 fills;
  (d) valve 526 is closed;
  (e) valve 532 is opened; and (f) heaters 528 are turned on, the heated fluid expands, and some fluid is forced into 510.

The sequence (a)-(f) may be repeated for continued pumping. One of skill in the art will note that the timing of the sequence steps may be adjusted. For example, (a) and (b) may be timed close together, or, if the pressure in channel 509 is not too high, then valve 532 may be closed before the heaters 528 are turned off. In this way, fluid in the mixing chamber 510 will not be drawn back into channel 509 as the fluid in 509 cools when the heaters 528 are turned off and the valve 532 is still open.

Microprocessor 520, by sensing the output of microfluidic measuring device 530, can control how fast to run sequence (a)-(f) and thus determine the amount of fluid transferred to the mixing chamber 510.

Figure 6:
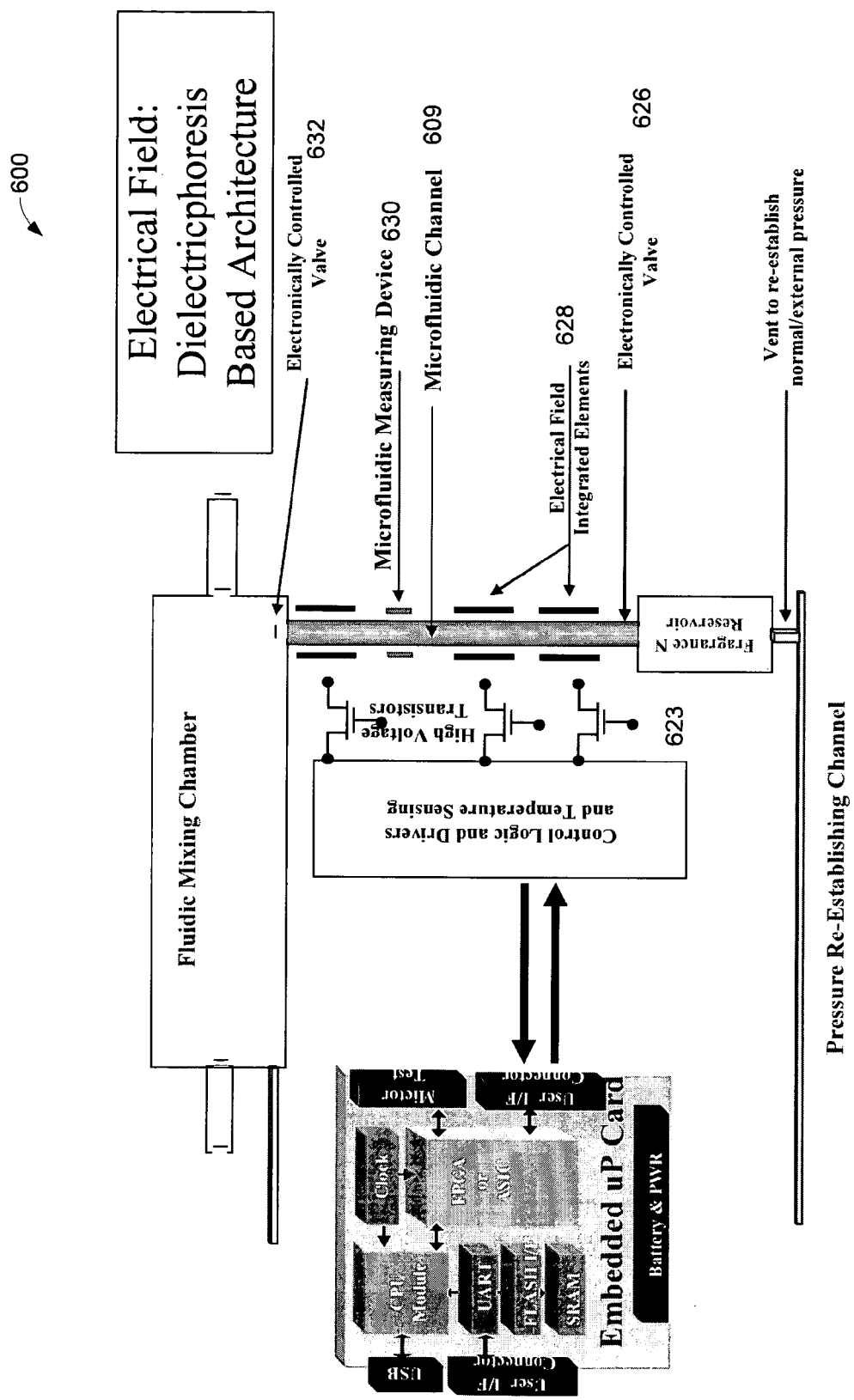
FIG. 6 illustrates one embodiment of the invention showing details for an electrical field dielectricphoresis-based architecture.

FIG. 6 illustrates one embodiment of the invention 600 showing details for an electrical field dielectricphoresis-based architecture. For illustration purposes only, a single fragrance reservoir is shown. A series of high voltage transistors 623 are connected to electrical field integrated elements 628. At 626 is an electronically controlled valve, at 609 a microfluidic channel, at 630 a microfluidic measuring device, and at 632 an electronically controlled valve.

FIG. 6 illustrates how an electrical field dielectricphoresis-based architecture may be used to move a fluid to a mixing chamber. For example, in one embodiment as illustrated in FIG. 6, fluid is moved as follows. The microprocessor controls the electrical field integrated elements 628 and the valves 626 and 632. The fluid in channel 609 has electrodynamic interactions, for example van der Waals and/or London forces that allow it to be moved by the electrodynamic effect.

One cycle of "pumping" may consist of the following:
(a) the high voltage to the electrical field integrated elements 628 are off;
(b) valve 632 is opened;
(c) valve 626 is opened and channel 609 starts filling;
(d) valve 626 is left open;
(e) valve 632 is left open; and
(f) the high voltage to the electrical field integrated elements 628 are turned on and pulsate in sequence, inducing the fluid to move toward the mixing chamber.

The sequence (a)-(f) may be repeated for continued pumping. One of skill in the art will note that the timing of the sequence steps may be adjusted.

The microprocessor, by sensing the output of microfluidic measuring device 630, can control how fast to run sequence (f) and thus determine the amount of fluid transferred to the mixing chamber. As the computed dose is transferred to the mixing chamber, valves 632 and 626 are closed, and elements 628 are turned off.

Figure 7:
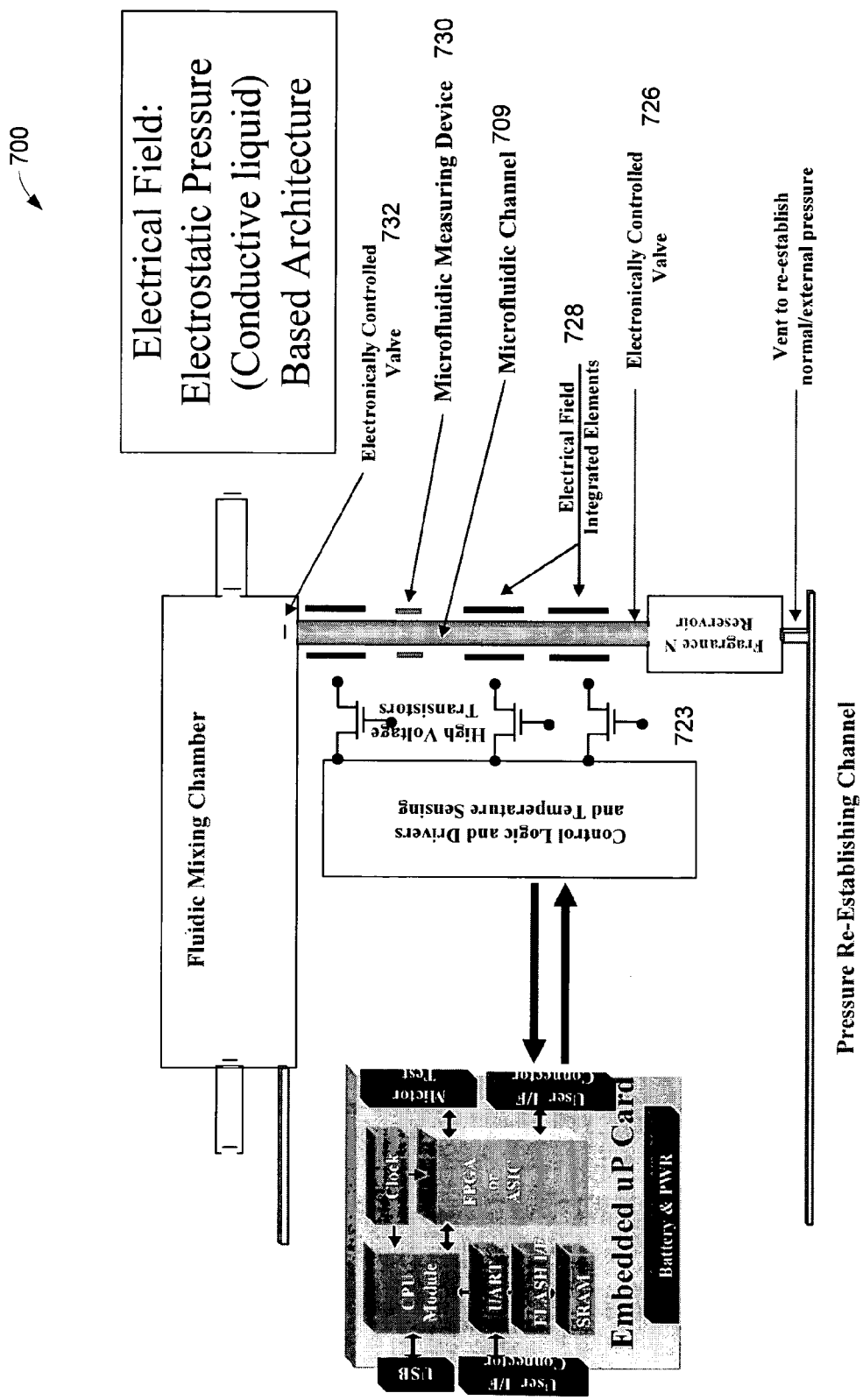
FIG. 7 illustrates one embodiment of the invention showing details for an electrical field electrostatic-based architecture.

FIG. 7 illustrates one embodiment of the invention 700, showing details for an electrical field electrostatic based architecture. For illustration purposes only, a single fragrance reservoir is shown. A series of high voltage transistors 723 is connected to electrical field integrated elements 728. At 726 is an electronically controlled valve, such as, but not limited to, an electrostatic valve, at 709 a microfluidic channel, at 730 a microfluidic measuring device, and at 732 an electronically-controlled valve.

FIG. 7 illustrates how an electrical field electrostatic-based architecture may be used to move a fluid to a mixing chamber. For example, in one embodiment as illustrated in FIG. 7, fluid is moved as follows. A microprocessor controls the electrical field integrated elements 728 and the valves 726 and 732. The fluid in channel 709 is a conductive liquid and/or contains a percentage of carrier liquid, with polarized molecules, that can be moved by electrical pressure.

One cycle of "pumping" may consist of the following:
(a) the high voltage to the electrical field integrated elements 728 are turned off;
(b) valve 732 is opened;
(c) valve 726 is opened and channel 709 fills;
(d) valve 726 is left open;
(e) valve 732 is left open; and
(f) the high voltage to the electrical field integrated elements 728 is turned on and off with the electrical field rotating in sequence, inducing the fluid to move toward the mixing chamber.

The sequence (a)-(f) may be repeated for continued pumping. One of skill in the art will note that the timing of the sequence steps may be adjusted.

Additionally, the electrical field integrated elements 728 may in one embodiment be polarized with opposite electrical charges so that the fluid is both attracted to one set of electrical field integrated elements and repulsed from another set of electrical field integrated elements. In this way a push-pull force may be used to move the fluid.

The microprocessor, by sensing the output of microfluidic measuring device 730, can control how fast to run sequence (a)-(f) and thus determine the amount of fluid transferred to the mixing chamber. As the computed dose is transferred to the mixing chamber, valves 732 and 726 are closed, and elements 728 are turned off.

Figure 8:
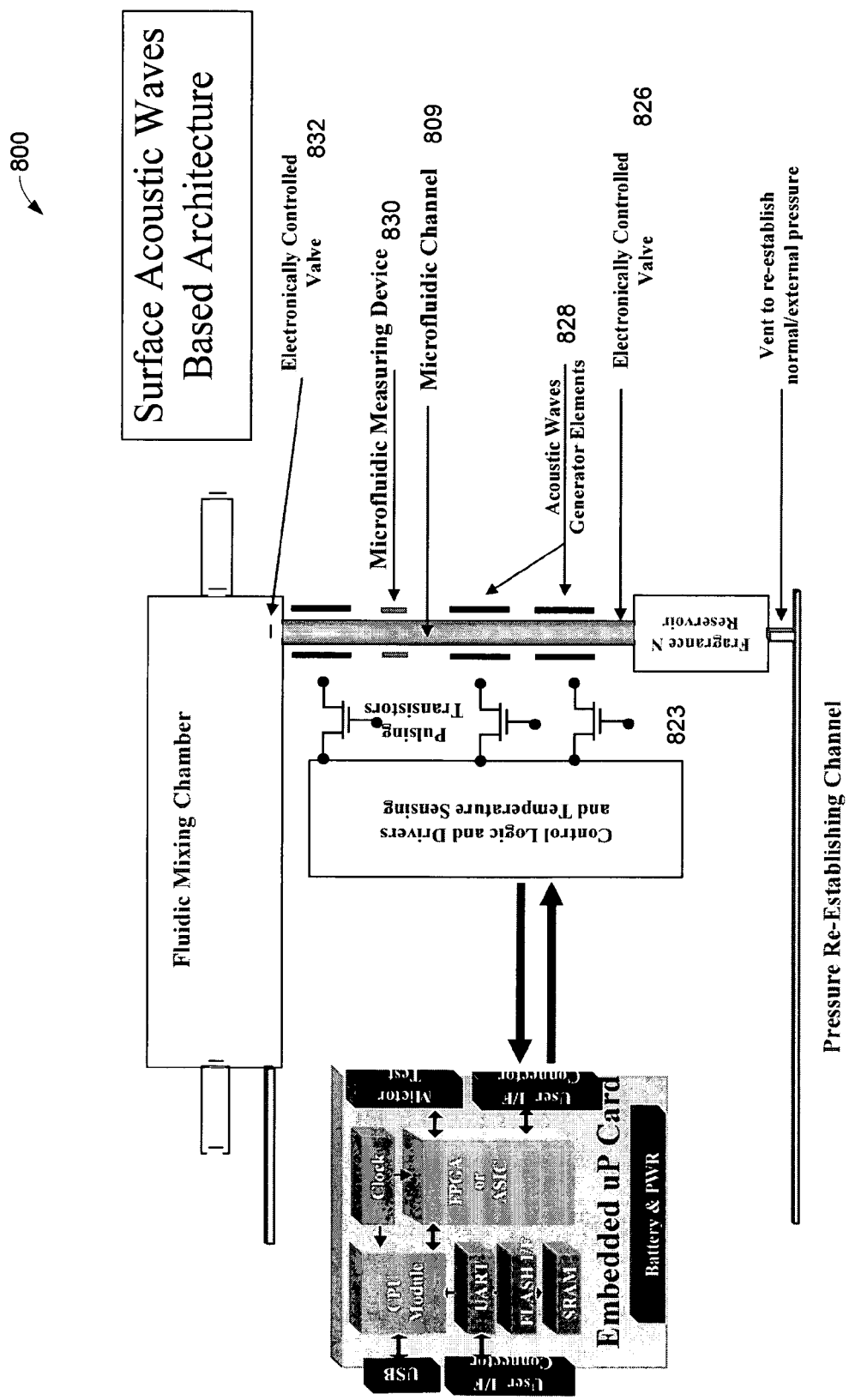
FIG. 8 illustrates one embodiment of the invention showing details for a surface acoustic wave-based architecture.

FIG. 8 illustrates one embodiment of the invention 800, showing details for a surface acoustic wave-based architecture. For illustration purposes only, a single fragrance reservoir is shown. A series of transistors for pulsing 823 are connected to acoustic wave generator elements 828. At 826 is an electronically controlled valve, at 809 a microfluidic channel, at 830 a microfluidic measuring device, and at 832 an electronically-controlled valve.

FIG. 8 illustrates how a surface acoustic wave-based architecture may be used to move a fluid to a mixing chamber. For example, in one embodiment as illustrated in FIG. 8, fluid is moved as follows. The microprocessor controls the acoustic wave generator elements 828 and the valves 826 and 832.

One cycle of "pumping" may consist of the following:
(a) the acoustic wave generator elements 828 are turned off;
(b) valve 832 is opened;
(c) valve 826 is opened and channel 809 fills;
(d) valve 826 is left open;
(e) valve 832 is alternatively opened to the rhythm of the transport wave or left open; and
(f) the acoustic wave generator elements 828 are turned on and off in sequence to create a transport wave, inducing the fluid to move toward the mixing chamber.

The sequence (a)-(f) may be repeated for continued pumping. One of skill in the art will note that the timing of the sequence steps may be adjusted.

The microprocessor, by sensing the output of microfluidic measuring device 830, can control how fast to run sequence (a)-(f) and thus determine the amount of fluid transferred to the mixing chamber. As the computed dose is transferred to the mixing chamber, valves 832 and 826 are closed and elements 828 are turned off.

Figure 9:
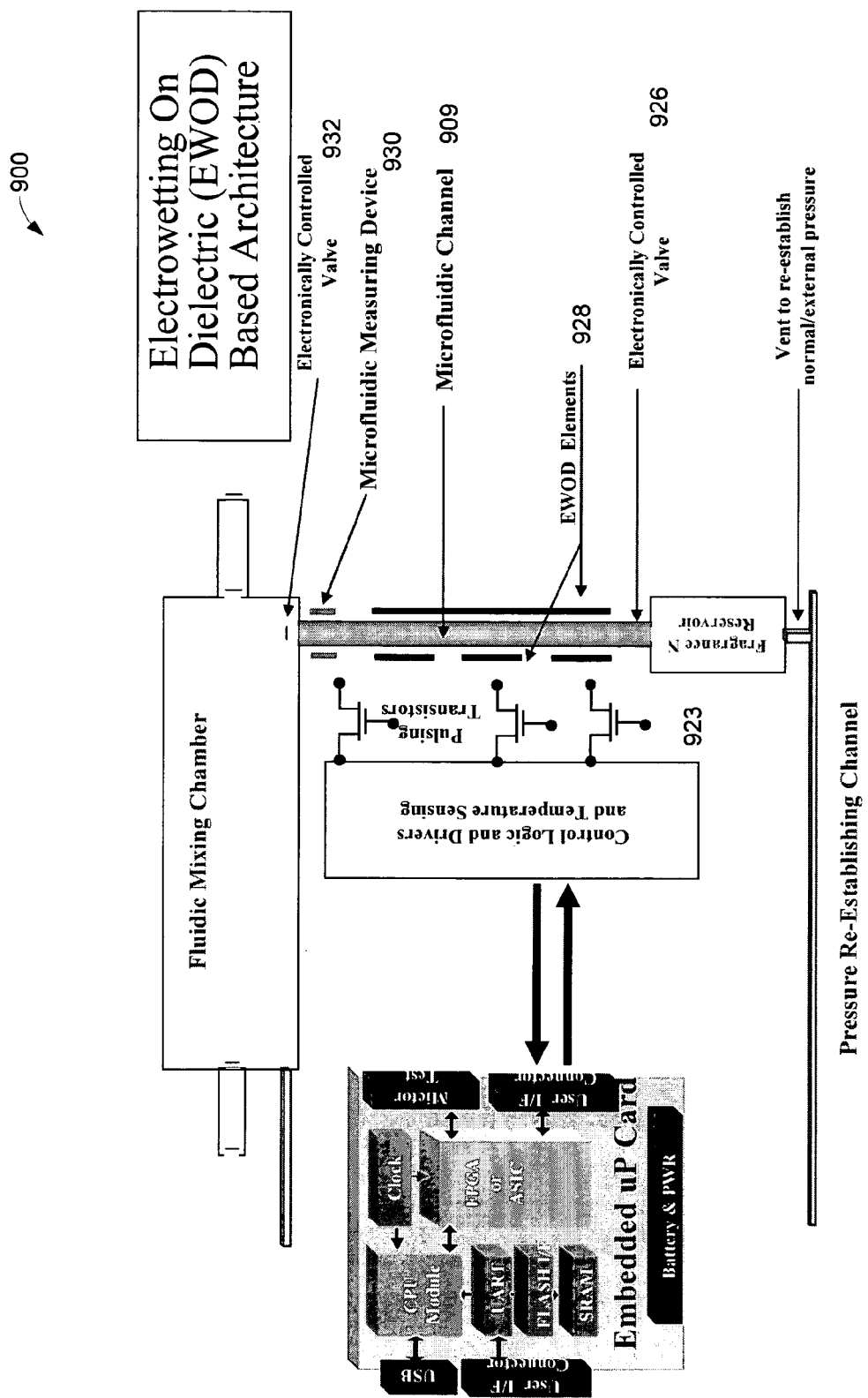
FIG. 9 illustrates one embodiment of the invention showing details for an electrowetting on dielectric-based architecture.

FIG. 9 illustrates one embodiment of the invention 900, showing details for an electrowetting on dielectric (EWOD)-based architecture. For illustration purposes only a single fragrance reservoir is shown. A series of transistors for pulsing 923 are connected to EWOD elements 928. At 926 is an electronically controlled valve, at 909 a microfluidic channel, at 930 a microfluidic measuring device, and at 932 an electronically-controlled valve.

FIG. 9 illustrates how an electrowetting on dielectric-based architecture may be used to move a fluid to a mixing chamber. For example, in one embodiment as illustrated in FIG. 9, fluid is moved as follows. The microprocessor controls the EWOD elements 928 and the valves 926 and 932.

One cycle of "pumping" may consist of the following:
(a) the EWOD elements 928 are off;
(b) valve 932 is opened;
(c) valve 926 is opened and channel 909 fills;
(d) valve 926 is left open;
(e) valve 932 is left open;
(f) the EWOD elements 928 are turned on and off in sequence, inducing the fluid to move toward the mixing chamber.

The sequence (a)-(f) may be repeated for continued pumping. One of skill in the art will note that the timing of the sequence steps may be adjusted.

The microprocessor, by sensing the output of microfluidic measuring device 930, can control how fast to run sequence (a)-(f) and thus determine the amount of fluid transferred to the mixing chamber. As the computed dose is transferred to the mixing chamber, valves 932 and 926 are closed and elements 928 are turned off.

Figure 10:
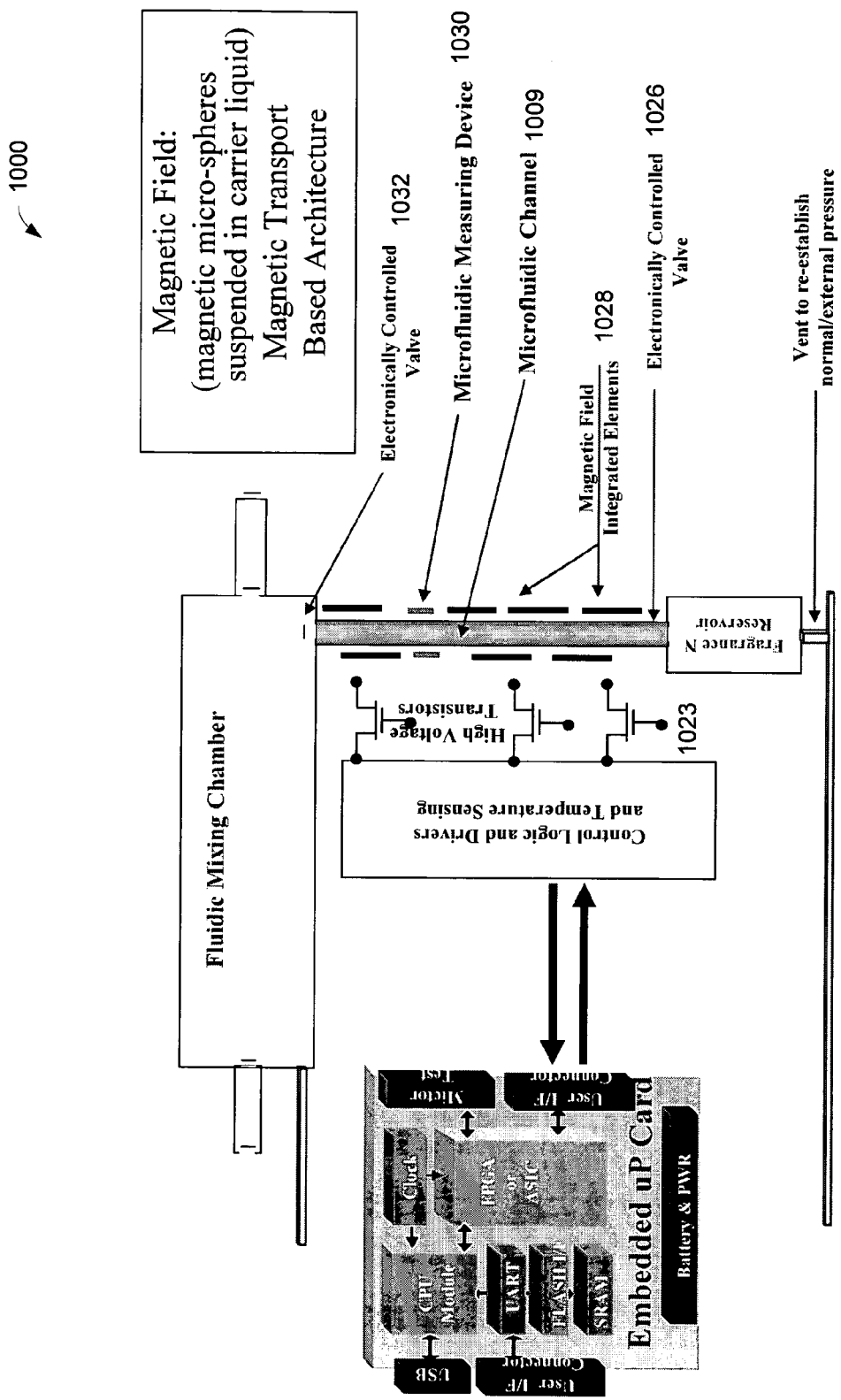
FIG. 10 illustrates one embodiment of the invention showing details for a magnetic field-based architecture.

FIG. 10 illustrates one embodiment of the invention 1000, showing details for a magnetic field-based architecture. For illustration purposes only, a single fragrance reservoir is shown. A series of transistors 1023 is connected to magnetic field integrated elements 1028. At 1026 is an electronically-controlled valve, at 1009 a microfluidic channel, at 1030 a microfluidic measuring device, and at 1032 an electronically-controlled valve.

FIG. 10 illustrates how a magnetic field-based architecture may be used to move a fluid to a mixing chamber. For example, in one embodiment as illustrated in FIG. 10, fluid is moved as follows. The microprocessor controls the magnetic field integrated elements 1028 and the valves 1026 and 1032.

One cycle of "pumping" may consist of the following:
(a) the magnetic field integrated elements 1028 are off;
(b) valve 1032 is opened;
(c) valve 1026 is opened and channel 1009 fills;
(d) valve 1026 is left open;
(e) valve 1032 is left open; and
(f) the magnetic field integrated elements 1028 are turned on and off in sequence, inducing the fluid to move toward the mixing chamber.

The sequence (a)-(f) may be repeated for continued pumping. One of skill in the art will note that the timing of the sequence steps may be adjusted.

The microprocessor, by sensing the output of microfluidic measuring device 1030, can control how fast to run sequence (a)-(f) and thus determine the amount of fluid transferred to the mixing chamber. As the computed dose is transferred to the mixing chamber, valves 1032 and 1026 are closed and elements 1028 are turned off.

One of skill in the art will appreciate that a magnetic-based transport requires that the original fragrances, chemicals, molecules, and/or compounds, etc. be charged or mixed with submicron- or micron-sized spheres of magnetic material. These spheres, of ferrous materials, for example iron or nickel, or other materials that can be magnetized or may have magnetic properties. These may help in transporting large-sized molecules or cells, for example, natural fragrances, perfume made up of molecules, pharmaceuticals, or other compounds for delivery of other personalized products.

Figure 11:
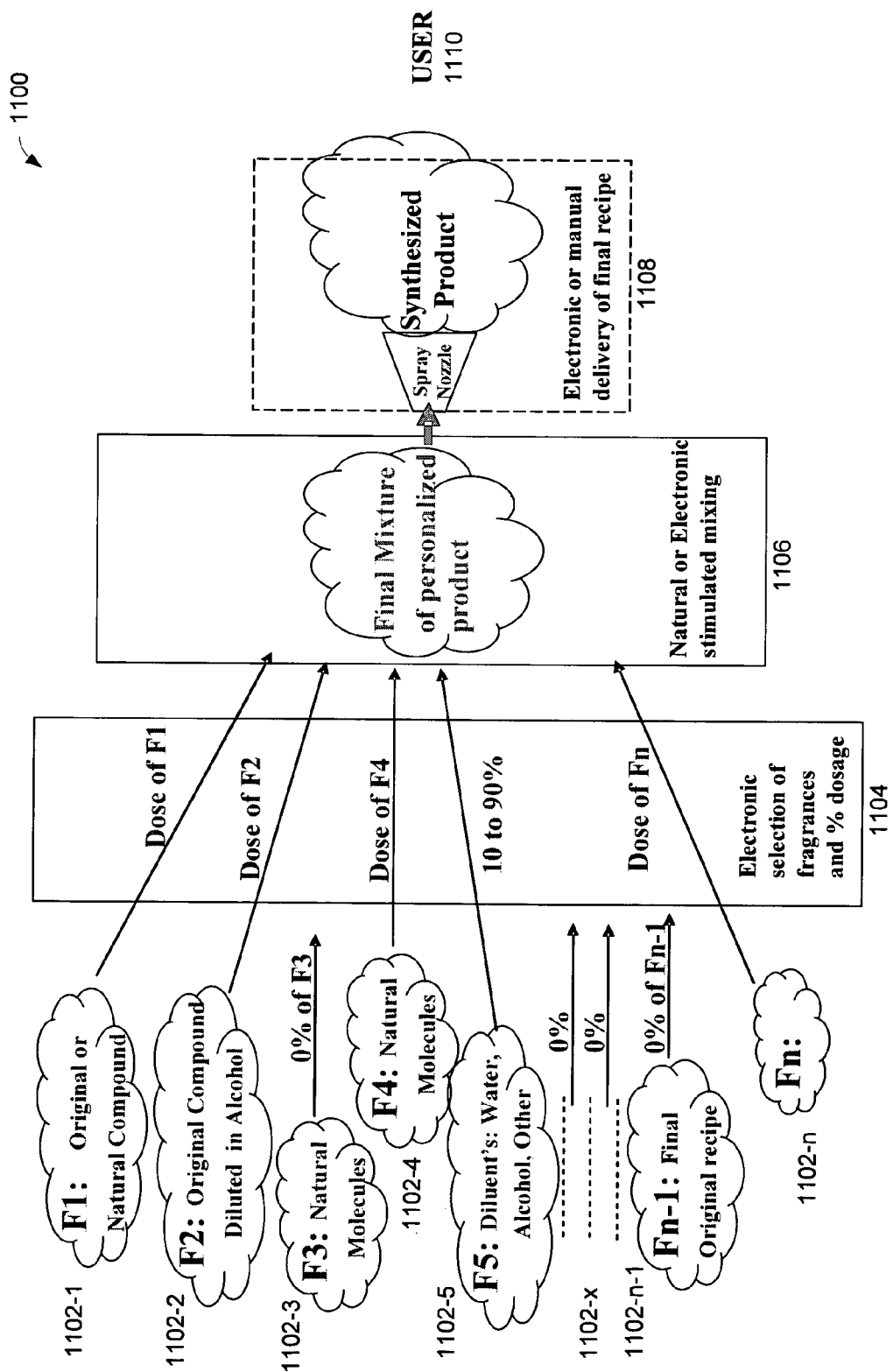
FIG. 11 illustrates one embodiment of the invention showing details for combining a variety of compounds.

FIG. 11 illustrates one embodiment of the invention 1100, showing details for combining a variety of compounds. Here a variety of compounds F1, F2, F3, F4, F5, Fn−1 and Fn (1102-1, 1102-2, 1102-3, 1102-4, 1102-5, 1102-n−1, and 1102-n, respectively) are available for mixing. At 1104, dosages are selected and in the present example, doses for F1, F2, F4, F5, and Fn are selected. Note that F3 and Fn−1, and those at 1102-x are not used. At 1106 a final mixture is prepared and at 1108 the mixture is delivered to a user 1110. The delivery 1108 as illustrated here, but the invention is not so limited, is a spray nozzle.

Note that the delivery of a mixture is not limited to liquid form only. Solids, powders, and gases may be dissolved and carried by a liquid or gaseous carrier as well, using the same principles described herein for liquids. For example, a sample may be prepared within the PPDD by mixing chemicals and/or cells and the PPDD may be used to study the sample for medical research, a drug study, and/or drug analysis. The PPDD may then be cleaned and reused to make and study other samples. The PPDD cleaning may for example be done by external mechanical means such as ultrasonic cleaning, physical mechanical cleaning, or may be cleaned by using cleaning compounds routed through the reservoirs, mixing chamber, nozzle, etc. of the PPDD.

As illustrated in FIG. 11, one of skill in the art will appreciate that the present invention may take various original elements, compounds, and/or natural molecules, etc and mix them to produce an instant useful product. For example, the techniques discussed for the present invention could be applied to drug delivery and other personalized products, such as, but not limited to, biological agents, chemicals, fragrances, perfumes, pharmaceutical compounds, wines, hair coloring compositions, dyes, implantable delivery systems, etc.

Figure 12:
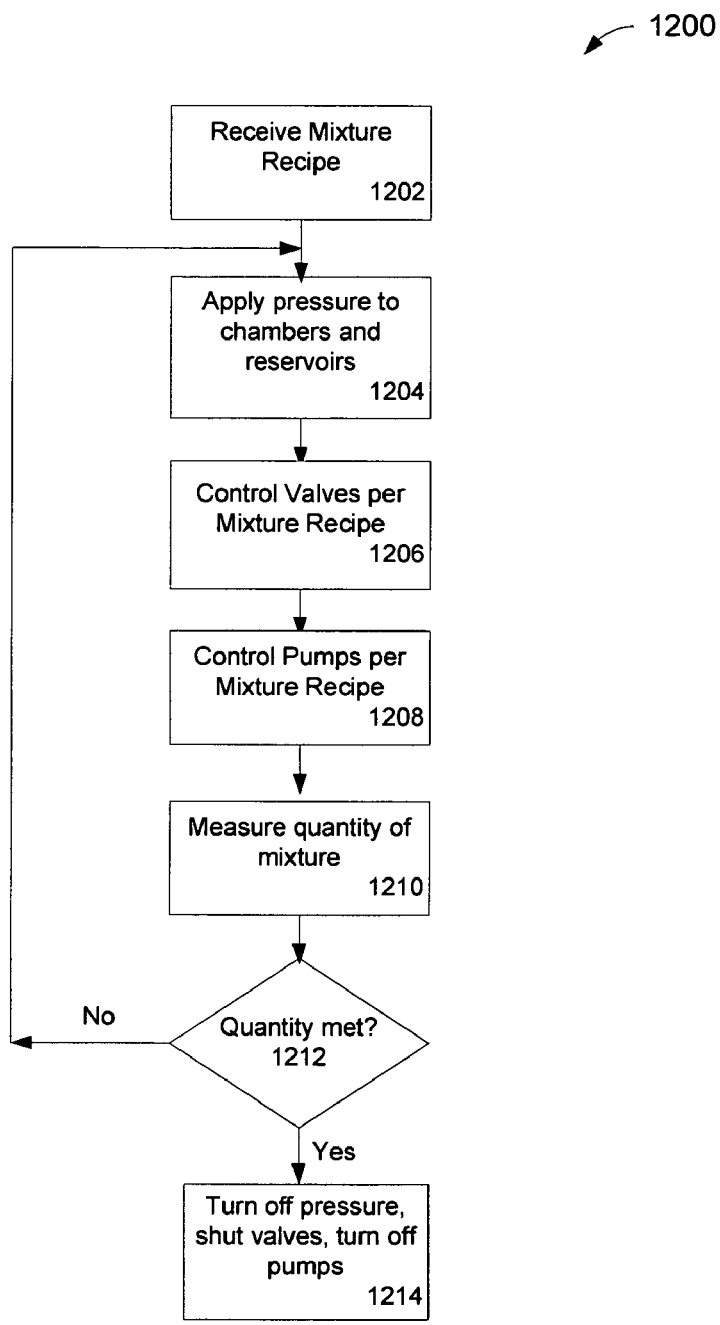
FIG. 12 illustrates one embodiment of the invention in flow diagram form.

FIG. 12 illustrates one embodiment of the invention 1200 in flow diagram form. At 1202 a mixture recipe is received. At 1204 pressure is applied to chambers and reservoirs. At 1206 valves are controlled in accordance with the mixture recipe. At 1208, pumps are controlled in accordance with the mixture recipe. At 1210, the quantity of the mixture is measured and at 1212 a determination is made to see if the correct amount of product, as specified by the recipe, has been made. If not, the process continues at 1204. If the quantity is sufficient, the pressure is turned off at 1214, the valves at 1206 are shut, and the pumps at 1208 are turned off.

A processing system such as that in FIG. 2 or a microprocessor such as that in FIG. 5 at 520 can control the valves, pumps, and pressure per the recipe. One of skill in the art will appreciate that if there are, say 5, 20 or 100 or more reservoirs, then depending upon the recipe, some reservoirs may not be used, some may hold similar contents, some may hold different contents. One of skill in the art will also appreciate that many combinations of mixtures are possible.

Mention has been made of a microfluidic measuring device, seen, for example, at 530, 630, 730, 830, and 930. One of skill in the art will appreciate that there are many ways to measure fluid flow. For example, by decreased pressure due to the Bernoulli effect, fluid flow may be measured by measuring pressure, by listening to vortices in a fluid, by measuring a Doppler effect, by observing light interruption due to a vane in the fluid, etc.

Mention has also been made of pumps and mixers above, however the invention is not so limited, and it is to be understood that other pump mechanisms and mixers may be used. For example, piezoelectric pumps, electrokinetic pumps, frequency modulated electrokinetic pumps, electroosmotic micropumps, micro injectors, ring electrokinetic chaotic micromixers, etc. may also be used.

The invention in various embodiments may have capabilities including, but not limited to: a delivery mechanism capable of mixing together natural, human-made, and synthetic chemicals, molecules, and other biological matter to be delivered as finished products; natural, human-made, and synthetic chemicals, molecules, and other biological matter may be combined according to a recipe(s); the combinations of dosed natural, human-made, and synthetic chemicals, molecules, and other biological matter made according to a recipe or several recipes may be used to deliver a product or several products; a user may be provided the possibility of developing their own "creation" or define experimentally by trial and error the best combination or a suitable combination of natural, human-made, and synthetic chemicals, molecules, and other biological matter into a deliverable product or products; providing to the user the possibility of developing their own "creation" and building a database of recipes or best combination or suitable combination of natural, human-made, and synthetic chemicals, molecules, and other biological matter to make into a deliverable product or products and such combinations can be recalled from memory and/or communicated to others.

For example, in one embodiment, the PPDD would allow personal creation of products that can be combined into the delivery mechanism, mixed, and delivered at the user's discretion. The creations and recipes can be uploaded into the PPDD Delivery System and used to create products at the user's discretion. Creations and recipes can be transmitted electronically to another party for experimenting or experiencing the same sensations remotely.

Additionally, the PPDD may contain radio frequency identification tags (RFID) for identifying compounds, or they may be mixed with the compounds. In this way a mixture having microscopic RFID tags may be used to indicate a variety of data, such as, but not limited to, the source of the compounds, the mixture ratio, etc. Chemical or molecular markers may also be used.

Thus a method and apparatus for personal product delivery have been described.

Referring back to FIG. 1, FIG. 1 illustrates a network environment 100 in which the techniques described may be applied. A plurality of computer systems are shown in the form of M servers (110-1 through 110-M), and N clients (120-1 through 120-N), which are coupled to each other via network 130. A plurality of terrestrial-based wireless communications links are shown in the form of T towers (140-1 through 140-T). A plurality of space based communications links are shown as S satellites (150-1 through 150-S). A plurality of personal communication devices are shown in the form of C cell phones (160-1 through 160-C). The M servers and N clients may also be coupled to each other via space based communications links 150-1 through 150-S, as well as terrestrial based wireless communications links 140-1 through 140-T, or a combination of satellite and terrestrial wireless links. Additionally, the C cell phones 160-1 through 160-C may be in communication with the satellites 150-1 through 150-S and/or the terrestrial wireless links 140-1 through 140-T.

Servers 110-1 through 110-M may be connected to network 130 via connections 112-1 through 112-M, respectively. Servers 130-1 through 130-M may be connected to the terrestrial links 140-1 through 140-T via antennae 114-1 through 114-M, respectively. Servers 110-1 through 110-M may be connected to space based communications links 150-1 through 150-S via dish antennae 116-1 through 116-M. Clients 120-1 through 120-N may be connected to the network 130 via connections 122-1 through 122-N. Clients 120-1 through 120-N may be connected to the terrestrial links 140-1 through 140-T via antennae 124-1 through 124-N.

Clients 120-1 through 120-N may be connected to space-based communications links 150-1 through 150-S via dish antennae 126-1 through 126-N. Cell phones 160-1 through 160-C may be connected to the terrestrial links 140-1 through 140-T and/or space-based communications links 150-1 through 150-S via antennae on each respective cell phone. Clients 120-1 through 120-N may also be connected to web sites, search engines, and/or database resources represented by servers, such as servers 110-1 through 110-M, via the network 130, through connections 122-1 through 122-N.

Clients 120-1 through 120-N may consist of, but are not limited to, for example, a desktop computer, a wireless laptop computer, a set-top box, a receiver, a television, a game platform, or other receiving devices. Applications may be running on the clients 120-1 through 120-N, while web pages and information being browsed may reside on the servers 110-1 through 110-M. Broadcasts may be coming from terrestrial sources 140-1 through 140-T, and/or satellite links 150-1 through 150-S. For purposes of explanation only, a single client 120-1 and a single car 160-1 will be considered to illustrate one embodiment of the present techniques. It will be readily apparent that such techniques may be easily applied to multiple clients and cars.

Network 130 may be a Wide Area Network (WAN), which includes the Internet, or other proprietary networks, such as America Online®, CompuServe®, Microsoft Network©, and Prodigy®. Note that alternatively, the network 130 may include one or more of a Local Area Network (LAN), modem links, satellite link, fiber network, cable network, or any combination of these and/or others. Network 130 may also include network backbones, long-haul telephone lines, Internet service providers, and various levels of network routers. Terrestrial links 140-1 through 140-T may be, for example, wireless cellular telephone service providers. Space-based communications links 170-1 through 170-S may be, for example, satellite broadcasters, global positioning satellites (GPS), etc. Communications networks for the present invention may be implemented in any number of environments.

Referring back to FIG. 2, FIG. 2 illustrates a processing system 200 in block diagram form, which may be representative of a control system for the PPDD, as well as a generalized computer processing system for controlling and/or interacting with a PPDD. The block diagram is a high level conceptual representation and may be implemented in a variety of ways and by various architectures. Bus system 202 interconnects a Central Processing Unit (CPU) 204, Read Only Memory (ROM) 206, Random Access Memory (RAM) 208, storage 210, display 220, audio, 222, keyboard 224, pointer 226, miscellaneous input/output (I/O) devices 228, and communications 230. The bus system 202 may be, for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (FireWire), Universal Serial Bus (USB), etc. The CPU 204 may be, for example, a single, multiple, or even a distributed computing resource. Storage 210 may be, for example, one or more Compact Disc (CD), Digital Versatile Disk (DVD), hard disks (HD), optical disks, tape, flash, memory sticks, video recorders, etc. Display 220 may be, for example, a Cathode Ray Tube (CRT), a Liquid Crystal Display (LCD), a projection system, Television (TV), etc. Note that depending upon the actual implementation of a computer system, the computer system may include some, all, more, or a rearrangement of components in the block diagram. For example, a thin client might consist of a wireless hand held device that lacks, for example, a traditional keyboard. Thus, many variations on the system of FIG. 2 are possible.

As used in this description, "personal communication devices" or similar phrases are to be understood to refer to devices capable of sending and/or receiving information, such as, but not limited to, personal digital assistants (PDAs), cell phones, personal organizers, pagers, wireless laptop computers, desktop computers, as well as machines capable of sending and/or receiving information such as, but not limited to, faxes, email, instant messages, etc.

Use of the word "compound", "compounds", or similar phrases are to be understood to refer to basic elements (from the periodic table), molecules, molecular compounds, chemicals, chemical compounds, or any combination and/or mixtures of these. Thus compounds include, but are not limited to, basic elements, gases, cells, natural or man-made fragrances, perfumes made up of molecules, pharmaceuticals, biological matter, synthetic chemicals, etc., and mixtures of these.

For purposes of discussing and understanding the invention, it is to be understood that various terms are used by those knowledgeable in the art to describe techniques and approaches. Furthermore, in the description, for purposes of explanation, numerous specific details are set forth in order to provide a thorough understanding of the present invention. It will be evident, however, to one of skill in the art, that the present invention may be practiced without these specific details. In some instances, well-known structures and devices are shown in block diagram form, rather than in detail, in order to avoid obscuring the present invention. These embodiments are described in sufficient detail to enable those of skill in the art to practice the invention, and it is to be understood that other embodiments may be utilized and that logical, mechanical, electrical, and other changes may be made without departing from the scope of the present invention.

Some portions of the description may be presented in terms of algorithms and symbolic representations of operations on, for example, data bits within a computer memory, and/or logic circuitry. These algorithmic descriptions and representations are the means used by those of skill in the arts to most effectively convey the substance of their work to others of skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities.

Further, any of the methods according to the present invention can be implemented in hard-wired circuitry, by programmable logic, or by any combination of hardware and software.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, or mathematical expression. Thus, one of skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software.

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

Thus a method and apparatus for personal product delivery have been described.

What is claimed is:

1. A mixing apparatus comprising:
a first air pump having a first pressurized output and a second pressurized output;
a plurality of reservoirs each having an input and an output, wherein each of said plurality of reservoirs input is directly connected to said first air pump first pressurized output;
a diluent reservoir having an input and an output, wherein said diluent reservoir input is directly connected to said first air pump second pressurized output;
a fluidic mixing chamber having a diluent reservoir input, an air pump input, a plurality of reservoir inputs, and an output, wherein each one of said fluidic mixing chamber plurality of reservoir inputs is connected to a single one of each of said plurality of reservoirs output through two intervening valves, and wherein said diluent reservoir output is connected to said fluidic mixing chamber diluent reservoir input through two diluent intervening valves, and wherein said fluidic mixing chamber air pump input is connected directly to said first air pump second pressurized output;
an accumulation chamber having a first input, a second input, and an output, wherein said accumulation chamber first input is connected to said fluidic mixing chamber output through two fluidic mixing chamber intervening valves, and wherein said accumulation chamber output is connected to a spray nozzle; and
a second air pump having a pressurized output, wherein said second air pump pressurized output is connected to said accumulation chamber second input through two second air pump intervening valves.

2. The mixing apparatus of claim 1 wherein one of said two intervening valves is fluidically situated proximate to each of said plurality of reservoirs output.

3. The mixing apparatus of claim 2 wherein one of said two diluent intervening valves is fluidically situated proximate to said diluent reservoir output.

4. The mixing apparatus of claim 3 wherein one of said two fluidic mixing chamber intervening valves is situated proximate to said fluidic mixing chamber output.

5. The mixing apparatus of claim 4 wherein one of said two second air pump intervening valves is situated proximate to said second air pump pressurized output.

* * * * *